(12) United States Patent
Beckmann et al.

(10) Patent No.: US 7,161,053 B2
(45) Date of Patent: *Jan. 9, 2007

(54) OLIGOMERIZATION OF ISOBUTENE IN N-BUTENIC HYDROCARBON STREAMS

(75) Inventors: Andreas Beckmann, Recklinghausen (DE); Franz Nierlich, Marl (DE); Udo Peters, Marl (DE); Wilfried Büschken, Haltern am See (DE); Lothar Kerker, Dülmen (DE); Dietrich Maschmeyer, Recklinghausen (DE); Dirk Röttger, Recklinghausen (DE)

(73) Assignee: Oxeno Olefinchemie GmbH, Marl (DE)

( * ) Notice: Subject to any disclaimer, the term of this patent is extended or adjusted under 35 U.S.C. 154(b) by 166 days.

This patent is subject to a terminal disclaimer.

(21) Appl. No.: 10/634,894

(22) Filed: Aug. 6, 2003

(65) Prior Publication Data

US 2004/0097773 A1    May 20, 2004

(30) Foreign Application Priority Data

Aug. 6, 2002  (DE) .............................. 102 35 934
Feb. 13, 2003 (DE) .............................. 103 06 214

(51) Int. Cl.
C07C 2/02 (2006.01)
C07C 2/04 (2006.01)
C07C 2/24 (2006.01)

(52) U.S. Cl. ...................... 585/530; 585/510; 585/516; 585/520

(58) Field of Classification Search .............. 585/510, 585/516, 520, 530
See application file for complete search history.

(56) References Cited

U.S. PATENT DOCUMENTS

| | | | |
|---|---|---|---|
| 3,518,323 A | 6/1970 | Pine et al. | |
| 3,531,539 A | 9/1970 | Tidwell | |
| 3,832,418 A | 8/1974 | Bercik et al. | |
| 4,100,220 A | 7/1978 | Bowman et al. | |
| 4,197,185 A | 4/1980 | Le Page et al. | |
| 4,313,016 A * | 1/1982 | Manning .................... | 585/832 |
| 4,375,576 A | 3/1983 | Smith, Jr. | |
| 4,447,668 A | 5/1984 | Smith, Jr. et al. | |
| 4,720,600 A | 1/1988 | Beech, Jr. et al. | |
| 5,003,124 A | 3/1991 | Smith, Jr. et al. | |
| 5,177,282 A | 1/1993 | Nierlich et al. | |
| 5,177,289 A * | 1/1993 | Smith et al. ................ | 585/526 |
| 5,723,687 A | 3/1998 | Marchionna et al. | |
| 5,877,372 A | 3/1999 | Evans et al. | |
| 5,994,601 A | 11/1999 | Nierlich et al. | |
| 6,274,783 B1 | 8/2001 | Gildert et al. | |
| 2002/0002316 A1 | 1/2002 | Girolamo et al. | |
| 2004/0097773 A1 | 5/2004 | Beckmann et al. | |
| 2004/0260113 A1 | 12/2004 | Bueschken et al. | |
| 2005/0038285 A1 | 2/2005 | Maschmeyer et al. | |
| 2005/0101800 A1 | 5/2005 | Buschken et al. | |
| 2006/0036121 A1 | 2/2006 | Kaizik et al. | |
| 2006/0041167 A1 | 2/2006 | Grass et al. | |

FOREIGN PATENT DOCUMENTS

| | | |
|---|---|---|
| DE | 2 223 513 | 11/1972 |
| DE | 28 53 769 | 6/1980 |
| DE | 29 44 457 | 5/1981 |
| EP | 0 048 893 | 4/1982 |
| EP | 0 224 220 | 6/1987 |
| EP | 0 325 144 | 7/1989 |
| EP | 0 417 407 | 3/1991 |
| EP | 0 536 839 | 4/1993 |
| EP | 1 074 534 | 2/2001 |
| GB | 2 057 006 | 3/1981 |
| GB | 2 325 237 | 11/1998 |
| WO | WO 93/06926 | 4/1993 |
| WO | WO 01/51435 | 7/2001 |
| WO | WO 01/81278 | 11/2001 |
| WO | WO 02/064531 | 8/2002 |

OTHER PUBLICATIONS

G. Scharfe, Hydrocarbon Processing, pp. 171-173, "Convert Butenes to High Octane Oligomers", Apr. 1973.
B. Schleppinghoff, Erdöl und Kohle-Erdgas-Petrochemie vereinigt mit Brennstoff-Chemie, vol. 27, No. 5, pp. 240-245, "Die Gewinnung Von $C_4$-Fraktionen Aus Äthylenanlagen Und Die Technologie Der Verarbeitung Von $C_4$-Kohlenwasserstoffen", May 1974.
M. J. Tsai, et al., Hydrocarbon Processing, pp. 81-87, "Consider New Technologies to Replace MTBE", Feb. 2002.
K. Weissermel, et al., Industrielle Organische Chemie, Wiley-VCH, 5th Edition, pp. 22-25, 65-99 and 118-125, 1998.
U.S. Appl. No. 10/790,706, filed Mar. 3, 2004, Beckmann et al.
U.S. Appl. No. 10/805,256, filed Mar. 22, 2004, Beckmann et al.
U.S. Appl. No. 10/790,707, filed Mar. 3, 2004, Beckmann et al.
U.S. Appl. No. 10/487,950, filed Mar. 5, 2004, Beckmann et al.
U.S. Appl. No. 10/634,894, filed Aug. 6, 2003, Beckmann et al.
U.S. Appl. No. 10/543,148, filed Jul. 25, 2005, Peters et al.
U.S. Appl. No. 10/519,397, filed Jan. 3, 2005, Obenaus et al.
U.S. Appl. No. 10/511,595, filed Nov. 2, 2004, Grass et al.
U.S. Appl. No. 10/579,471, filed May 15, 2006, Zanthoff et al.

* cited by examiner

Primary Examiner—Glenn Caldarola
Assistant Examiner—In Suk Bullock
(74) Attorney, Agent, or Firm—Oblon, Spivak, McClelland, Maier & Neustadt, P.C.

(57) ABSTRACT

Isobutene in isobutenic hydrocarbon mixtures is oligomerized over a solid acidic ion exchange resin, said acidic ion exchange resin containing, for example, sulfonic acid groups, some of whose protons have been exchanged for metal ions.

17 Claims, No Drawings

OLIGOMERIZATION OF ISOBUTENE IN N-BUTENIC HYDROCARBON STREAMS

BACKGROUND OF THE INVENTION

1. Field of the Invention

The present invention relates to a process for oligomerizing isobutene an isobutenic hydrocarbon mixture over a solid acidic ion exchange resin, said acidic ion exchange resin containing sulfonic acid groups, some of whose protons have been exchanged for metal ions.

2. Discussion of the Background

A mixture of 2,4,4-trimethylpent-1-ene and 2,4,4-trimethylpent-2-ene, usually referred to in industry as diisobutene, is obtained on an industrial scale by dimerizing isobutene. Especially after hydrogenation to the corresponding paraffin (isooctane, 2,2,4-trimethylpentane), it is a sought-after fuel component owing to its high octane number (a measure of the knock resistance of the carburetor fuel). Isooctane also serves as a reference for determining the octane number. For use as a fuel additive, mixtures of diisobutene or isooctane can also be used which contain other $C_8$ isomers or hydrocarbons having other carbon numbers.

For use in syntheses, relatively high purities of the diisobutene are normally desired. Hydroformylation of diisobutene provides 3,5,5-trimethylhexanal which can be oxidized to the corresponding carboxylic acid. The carboxylic acid finds use for preparing peroxides, lubricants and siccatives. Diisobutene is also used for alkylating phenols. The resulting alkylaromatics are intermediates for the production of detergents.

Diisobutene is obtainable by the dimerization, generally oligomerization, of isobutene. In addition to the dimers ($C_8$), this also results in oligomers of higher molar masses (mainly $C_{12}$, $C_{16}$). As a result of framework rearrangement reactions, the $C_8$-dimers also contain small proportions of other $C_8$-olefins in addition to diisobutene. When the reactant used for the oligomerization is isobutene in mixtures with other olefins, cooligomers are additionally formed. In the presence of 1-butene, 2,2-dimethylhexenes and 2,2,3-trimethylpentenes, for example, are formed.

For the economic preparation of diisobutene, whether it be as a reactant for syntheses or as a fuel additive, from isobutenic hydrocarbon mixtures, several criteria are to be observed. These include a high $C_8$ selectivity, a high $C_8$ isomer purity, the long-term stability of the catalyst, the technical solutions for removing the heat of reaction generated and, in the case of mixtures which also contain 1-butene, a low isomerization of the 1-butene to 2-butenes.

Among other reasons, a high $C_8$ selectivity is desired, since the tetramers of isobutene (or cotetramers with linear $C_4$-olefins) or their hydrogenated derivatives are unsuitable for use in carburetor fuels, since they have too high a boiling point. The formation of tetramers in the preparation of fuel additives thus constitutes a real yield loss. The boiling points of the trimers and of the hydrogenated derivatives at 170–180° C. lie within the upper part of the boiling point range for carburetor fuels; although they can be used proportionately in fuels, their formation is nevertheless to be substantially minimized.

A high $C_8$ isomer purity, i.e. a high proportion of diisobutene in the $C_8$ fraction and only slight formation of codimers (dimer of 1-butene and isobutene) and rearrangement products, is desired especially in the preparation of diisobutene which finds use in syntheses. In addition, the formation of codimers with, for example, n-butenes is to be avoided, since this consumes n-butenes which could otherwise be used in other ways (1-butene, for example, as a (co)monomer for polymers).

High long-term stability of the catalysts is necessary not only to minimize the catalyst costs, but also to keep the technical cost and inconvenience of the catalyst change low.

The oligomerization of isobutene additionally releases heat in considerable amounts. When this is not removed to a sufficient extent, the reaction mixture heats up. This can lead both to deterioration in the selectivities and to an adverse effect on the catalyst stability.

Isobutene is often obtained industrially in mixtures with 1-butene. It is not possible to separate the materials by distillation at technically viable cost and inconvenience. A separation is therefore achieved by selective chemical reaction of one of the two components, for example etherification of the isobutene. However, the chemical conversion of the isobutene must not result in the rearrangement of the 1-butene to 2-butenes (cf. K. Weissermel, H. J. Arpe, Industrielle Organische Chemie, Wiley-VCH, $5^{th}$ Edition, 1998, page 74–82). 1-Butene is a sought-after raw material, and, among other uses, it is used as a comonomer in the preparation of polyolefins.

All of these criteria have already been addressed in the literature and some solutions have also been found. One of the main emphases of the work is in the development of catalysts. The oligomerization of isobutene can be catalyzed by Lewis or Bröonsted acids, or coordination compounds, in particular those of nickel. Catalysts for this reaction have been known for some time and are the subject-matter of numerous patents and publications.

The oligomerization can in principle be carried out homogeneously, i.e. using catalysts soluble in the reaction mixture, or heterogeneously, i.e. using catalysts insoluble in the reaction mixture. The disadvantage of the homogeneous process is that the catalyst leaves the reactor with the reaction products and unconverted reactants, from which it has to be removed, worked up and disposed of or recycled.

Most of the industrial processes therefore use heterogeneous catalysts which are additionally often arranged in a fixed bed, so that there is no need for a costly or inconvenient catalyst removal. Most of the existing fixed bed catalysts belong to one of the following groups:

a) mineral acids (e.g. sulfuric acid or phosphoric acid) on a support material (e.g. alumina or silica)

b) the zeolites or other aluminum silicates, undoped or doped by further metals, in particular with transition metals c) acidic ion exchange resins.

Mineral acids on supports have little suitability as catalysts, since they also promote framework rearrangements (reaction of two molecules of isobutene to give $C_8$-isomers other than 2,4,4-trimethylpentene).

In EP 0 224 220, a butene oligomerization is carried out over a zeolite catalyst doped with bismuth and/or lead. The $C_8$ fraction contains over 4% of undesired 2,3,4-trimethylpentenes. Zeolites are likewise used as catalysts in U.S. Pat. No. 4,720,600. The oligomerization of isobutene over an x-ray-amorphous aluminum silicate is disclosed in EP 0 536 839. Even at the mild temperatures of 60–65° C., it fails to avoid a loss of 2,2,4-trimethylpentenes by skeletal isomerization. Isobutene oligomerization over an x-ray-amorphous nickel aluminum silicate is described in WO 93/06926. This converts undiluted isobutene at 60° C. The product spectrum shows that the $C_8$ selectivity is not particularly high. At an isobutene conversion of 15–20%, the $C_8$ selectivity is 85–86%, and at a conversion of 75%, only 72%. In U.S. Pat. No. 3,531,539, isobutene which is in mixtures of 1-butene is converted over a molecular sieve. U.S. Pat. No. 3,518,323 discloses the conversion of isobutene which is in mixtures with n-butenes over a supported nickel catalyst. The selective dimerization of isobutene from mixtures of $C_4$-monoolefins over heterogeneous nickel catalysts is also described by U.S. Pat. No. 3,832,418. In U.S. Pat. No. 4,197,185, the conversion of isobutene from mixtures of $C_4$-hydrocarbons over inorganic heterogeneous catalysts is part of the claimed process.

The conversion of isobutene over acidic ion exchange resins has been known for some time and has also been used in industrial scale processes (Hydrocarbon processing, April 1973, page 171; Erdöl, Kohle, Erdgas, Petrochem. 1974, 27, Volume 5, page 240). The discussion on limiting the use of MTBE (methyl tert-butyl ether, obtained industrially from isobutene and methanol) as a fuel additive has led to processes for dimerizing isobutene again finding increased attention. For this reason, an up-to-date review of process variants for converting isobutene over acidic ion exchange resins has been published (Hydrocarbon Processing, February 2002, page 81). Depending on the isobutene content of the raw material used, different process variants are used, both in order to manage the exothermicity of the reaction, and in order to control the selectivity. The isobutene concentration is reduced mainly by adding moderators and/or diluting.

The use of moderators which are added to the reaction in order to control activity and selectivity of the catalyst is the subject-matter of various patents. Typical moderators are, for example, methyl tert-butyl ether, tert-butanol or water. The disadvantage in principle of moderators is that the moderator or subsequent products formed from it have to be removed from the product. U.S. Pat. No. 4,100,220 discloses the use of water or TBA (tert-butyl alcohol) as the moderator, while WO 01/51435 describes the use of TBA. U.S. Pat. Nos. 4,375,576 and 4,447,668 use MTBE as a moderator, GB 2325237 uses ethers and primary alcohols, EP 1074534 uses tertiary alcohols, primary alcohols and ethers, and EP 1074534 uses "oxygenates" in general. Since t-butyl ethers such as MTBE are formed from isobutene and alcohols in the presence of acidic catalysts, there also exist processes for parallel production of ethers and isobutene oligomers (U.S. Pat. No. 5,723,687).

The use of moderators additionally brings disadvantages in industrial operation. Catalysts used as ion exchangers whose activity is reduced by adding moderators such as water or TBA react very slowly on loading changes in the reactor. After the amount of feed is changed, the reactor requires time in order to return to a steady state. Steady state behavior of the reactor is advantageous for simple and safe operation of the plant. One advantage of the use of partly neutralized ion exchangers is that the time required to achieve steady state reactor behavior after a loading change is shortened.

In addition to or parallel to the use of moderators, the dilution of the isobutenic feedstock is described, in order to achieve better selectivities, but in particular control of the exothermicity (U.S. Pat. No. 5,877,372, WO 01/51435, US 2002/0002316). U.S. Pat. No. 5,003,124 describes a process in which the problem of removing the heat of reaction is countered by working only partly in the liquid phase at the boiling temperature of the liquid phase.

The documents U.S. Pat. No. 6,274,783 and WO 01/81278 both relate to processes for oligomerization with simultaneous hydrogenation of the products.

In EP 0 417 407, shaped bodies of strongly acidic ion exchangers are used as the catalyst for the oligomerization of isobutene. Some of the ion exchangers are subsequently treated with acid, in order to achieve increased acidity. The dimers yield of 93–96% is good. However, the composition of the $C_8$ fraction is not disclosed.

EP 0 048 893 describes a process for preparing $C_4$-oligomers and alkyl tert-butyl ethers. Isobutene is converted together with alcohols in the liquid phase over an acidic cation exchanger whose acidic sites are occupied by one or more metals of groups 7 or 8 of the Periodic Table. The metals are in elemental form.

EP 0 325 144 discloses the use of acidic ion exchangers which are partly laden with amphoteric elements (preference is given to aluminum, chromium, vanadium, titanium, zirconium, molybdenum, tungsten). These modified ion exchangers are used as catalysts in the preparation of tert-amyl alcohol (TAA) from i-amylenes. The advantages of the process are an increased conversion of the i-amylenes and simultaneous suppression of the oligomerization of the i-amylenes.

There is therefore a need for the efficient preparation of diisobutene, and the removal of isobutene to prepare 1-butene from $C_4$-hydrocarbon mixtures.

SUMMARY OF THE INVENTION

It is an object of the present invention, to provide a process for the efficient preparation of diisobutene, and the removal of isobutene to prepare 1-butene from $C_4$-hydrocarbon mixtures.

This and other objects have been achieved by the present invention the first embodiment of which includes a process for oligomerizing isobutene, comprising:

oligomerizing isobutene in the presence of n-butene over a solid, acidic ion exchanger having acidic protons;

wherein at least one acidic proton of said ion exchanger has been exchanged for a metal ion.

In another embodiment, the present invention provides for a process for preparing 1-butene from $C_4$-hydrocarbon comprising:

converting a $C_4$-hydrocarbon mixture over an acidic, solid ion exchanger having acidic protons;

wherein at least one acidic protons of said ion exchanger has been exchanged for a metal ion, thereby obtaining a reaction product; and wherein the 1-butene is removed from the reaction product by distillation.

DETAILED DESCRIPTION OF THE INVENTION

It has been found that, surprisingly, this object can be achieved by oligomerizing isobutene in the liquid phase over an acidic in exchange resin having sulfonic acid groups when some of the protons of the acidic ion exchanger have been exchanged for metal ions.

The present invention therefore provides a process for oligomerizing isobutene in the presence of n-butenes over a solid, acidic ion exchanger, wherein the conversion is carried out over an ion exchanger, some of whose acidic protons have been exchanged for metal ions.

This technique can also be used to efficiently obtain 1-butene. The present invention therefore further provides a process for preparing 1-butene from $C_4$-hydrocarbon mixtures, wherein the $C_4$-hydrocarbon mixtures are converted over an acidic, solid ion exchanger, some of whose acidic protons have been exchanged for metal ions, and the 1-butene is removed from the reaction product.

Acidic ion exchange resins can only be used as catalysts for the oligomerization of isobutene when they have a certain minimum acidity. For instance, resins having carboxylic acid groups are frequently not acidic enough and therefore generally unsuitable as catalysts. Suitable resins are those having sulfonic acid groups. Their activity in the oligomerization of isobutene can be reduced by moderators such as alcohols (TBA), ethers (MTBE) or water.

The literature discloses the reduction of the acid strength of ion exchangers having sulfonic acid groups by partial ion exchange (Structure-breaking Effect of Metal Ions influencing the Acidity of an Anhydrous Acid, C. Buttersack, H. Widdecke, J. Klein, Journal of Molecular Catalysis, 40 (1987) 23–25). However, it is surprising that an ion exchange resin modified in this way can advantageously be used in the preparation of fuel additives from isobutenic hydrocarbon mixtures.

The ion exchange resins used in the process according to the present invention are solid sulfonated ion exchange resins in which in particular from 0.1 to 60%, from 0.1 to 50%, from 0.1 to 40%, from 0.1 to 30%, from 0.1 to 29%, preferably form 0.5 to 20%, more preferably from 5 to 15%, of the acidic protons of the sulfonic acid groups have been exchanged for metal ions. The amount of acidic protons of the sulfonic acid groups which have been exchanged for metal ions includes all values and subvalues therebetween, especially including 0.5, 1, 2, 3, 4, 5, 10, 15, 20, 25, 30, 35, 40, 45, 50 and 55%.

Useful metal ions which replace the protons include alkali metal, alkaline earth metal, chromium, manganese, iron, cobalt, nickel, zinc and aluminum ions, and also ions of the lanthanide group (rare earths). For this purpose, preference is given to using alkali metal ions, in particular sodium ions. It is also possible that the resin is laden with two or more different metal ions.

Suitable ion exchange resins are, for example, those which are prepared by sulfonating phenol/aldehyde condensates or cooligomers of aromatic vinyl compounds. Examples of aromatic vinyl compounds for preparing the cooligomers are: styrene, vinyltoluene, vinylnaphthalene, vinylethylbenzene, methylstyrene, vinylchlorobenzene, vinylxylene and divinylbenzene. The cooligomers in particular which result from reaction of styrene with divinylbenzene are used as a precursor for the preparation of ion exchange resins having sulfo groups. The properties of these resins, in particular specific surface area, porosity, stability, swelling or shrinking and exchange capacity can be varied via the preparative process. The resins can be prepared in gel-like, macroporous or spongelike form. Strongly acidic resins of the styrene-divinylbenzene type are sold, inter alia, under the following trade names: CT 151 from Purolite, Amberlyst 15, Amberlyst 35, Amberlite IR-120, Amberlite 200 from Rohm&Haas, Dowex M-31 from DOW, K 2611, K 2431 from Bayer.

The ion exchange capacity of the resins fully in the $H^+$ form is typically between 1 and 2 mol, in particular from 1.5 to 1.9 mol, of $H^+$ per liter of moist resin (as obtained commercially). The ion exchange capacity of the resins includes all values and subvalues therebetween, especially including 1.1, 1.2, 1.3, 1.4, 1.5, 1.6, 1.7, 1.8 and 1.9 mol.

The resins used in the process of the present invention are preferably macroporous resins, for example K 2431 from Bayer, Amberlyst 15 or Amberlyst 35 from Rohm & Haas. The pore volume is preferably from 30 to 60 ml/g, in particular from 40 to 50 ml/g (based on commercially obtained water-moist resin). The pore volume includes all values and subvalues therebetween, especially including 35, 40, 45, 50 and 55 ml/g.

The particle size of the resin is preferably between 500 μm and 1500 μm, in particular between 600 μm and 1000 μm. The particle size of the resin includes all values and subvalues therebetween, especially including 600, 700, 800, 900, 1000, 1100, 1200, 1300 and 1400 μm.

A narrow or wide particle size distribution may be selected. For example, ion exchange resins having very uniform particle size (monodisperse resins) can be used.

It may be advantageous to use relatively large particles in reactors which are flowed through at high linear rates to reduce the pressure differential, and to use smaller particles in reactors which are flowed through at a low linear rate to achieve the optimum conversion.

Optionally, the ion exchange resins can be used as shaped bodies, for example cylinders, rings or spheres.

When a plurality of reactors is used, these may be charged with resin of the same or different particle sizes (or particle size distributions).

For the preparation of the partly neutralized ion exchange resins, various processes which are all described in the technical literature can be applied. When the ion exchange resin is in the H form, protons can be exchanged for metal ions. When the resin is in metal salt form, metal ions can be replaced by protons with the aid of acids. In principle, this ion exchange can be effected using organic or an aqueous suspension.

In a simple process, for example, the ion exchange resin in the $H^+$ form is slurried with sufficient liquid to obtain a readily stirrable suspension. A solution which contains the desired ions is added. After completed ion exchange, the partly exchanged ion exchange resin is washed and dried.

The amount of solvents to slurry the ion exchange resin is typically from one to ten times the intrinsic volume of the ion exchange resin. For the preparation of the solution of the desired type of ion which is metered in, it is advantageous to choose a solvent which is miscible with the solvent in which the resin is suspended. It is advantageous to use the same solvent.

The ion exchange is effected preferably within the temperature range from 10 to 100° C., more preferably from 20 to 40° C. The temperature includes all values and subvalues therebetween, especially including 15, 20, 25, 30, 35, 40, 45, 50, 55, 60, 65, 70, 75, 80, 85, 90 and 95° C. The exchange is generally complete after a maximum of 24 hours. After the ion exchange, the catalyst is separated from the solution, for example by decanting or filtering, and optionally subsequently washed with a solvent. It is advantageous to use the same solvent in which the catalyst was suspended.

It is advantageous to dry the moist catalyst, firstly to make it easier to handle (more free-flowing) and secondly to keep the contamination of the product by the adhering solvent or its subsequent products low in the first days after the startup of the reactor. The drying can be effected in a vacuum or in an inert gas stream, for example in a nitrogen stream. The drying temperatures are typically between 10 and 120° C. The drying temperature includes all values and subvalues therebetween, especially including 15, 20, 25, 30, 35, 40, 45, 50, 55, 60, 65, 70, 75, 80, 85, 90, 95, 100, 105, 110 and 115° C.

A preferred route for preparing the catalysts used in the process according to the present invention is the exchange of protons for metal ions in the aqueous phase, washing the partly exchanged ion exchange resin with water and subsequent drying.

The ions with which the resin is to be laden may be present as solutions of hydroxides, or salts of organic or inorganic acids. The salts of polybasic acids may also include acidic salts. It is likewise possible to use compounds of other organic radicals, for example alkoxides or acetylacetonates.

The sources used for the metal ions are preferably metal hydroxides and salts of inorganic acids. Very particular preference is given to using alkali metal hydroxides (e.g. sodium hydroxide), alkali metal halides (e.g. sodium chloride), alkali metal sulfates (e.g. sodium sulfate), alkali metal nitrates (e.g. sodium nitrate), alkaline earth metal hydroxides and alkaline earth metal nitrates.

The above-described procedure can be used to prepare catalysts of different activity and selectivity depending on the degree of exchange, type of ion and resin.

A reactor in the process according to the present invention may contain a mixture of resins of different reactivity. It is equally possible that a reactor contains catalysts having different activity, arranged in layers. When more than one reactor is used, the individual reactors may be charged with catalysts of the same or different activity or activities.

The starting materials used are isobutenic hydrocarbon mixtures. Preference is given to using mixtures of isobutene with other $C_4$-hydrocarbons (proportion of $C_4$ components greater than 95%).

Technical mixtures which contain isobutene are, for example, light benzine fractions from refineries, $C_4$ fractions from crackers (for example steam crackers, hydrocrackers, catalytic crackers), mixtures from Fischer-Tropsch syntheses, mixtures from the dehydrogenation of butanes, mixtures from skeletal isomerization of linear butenes and mixtures resulting from metathesis of olefins. These techniques are all described in the literature (K. Weissermel, H. J. Arpe, Industrielle Organische Chemie, Wiley-VCH, 5$^{th}$ Edition, 1998, pages 23–24; 65–99; 122–124).

Preference is given to using $C_4$ fractions from steam crackers (which are primarily operated to produce ethene and propene and in which the raw materials used are, for example, refinery gases, naphtha, gas oil, LPG (liquefied petroleum gas) and NGL (natural gas liquid)) or catalytic crackers. Depending on the cracking process, the $C_4$ cuts obtained as a by-product contain different amounts of isobutene. Further main constituents are 1,3-butadiene, 1-butene, c-2-butene, t-2-butene, n-butane and i-butane. Typical isobutene contents in the $C_4$ fraction are from 18 to 35% in the case of $C_4$ fractions from steam crackers, and 10–20% in the case of FCC catalytic crackers. The isobutene contents includes all values and subvalues therebetween, especially including 20, 22, 24, 26, 28, 30, 32 and 34% in the case of $C_4$ fractions from steam crackers. The isobutene contents includes all values and subvalues therebetween, especially including 12, 14, 16 and 18% in the case of FCC catalytic crackers.

It is advantageous for the process according to the present invention to remove polyunsaturated hydrocarbons such as 1,3-butadiene from the starting mixture. This can be effected by known processes, for example by extraction, extractive distillation or complex formation (cf. K. Weissermel, H. J. Arpe, Industrielle Organische Chemie, Wiley-VCH, 5$^{th}$ Edition, 1998, page 119–121).

An alternative to removal of the polyunsaturated hydrocarbons is a selective chemical conversion. For example, 1,3-butadiene can be selectively hydrogenated to linear butenes, as described, for example, in EP 52 3482. The 1,3-butadiene can also be at least partly removed by selective conversions of the 1,3-butadiene, for example dimerization to cyclooctadiene, trimerization to cyclododecadiene, polymerization or telomerization reactions. When the raw material used was a crack $C_4$ cut, a hydrocarbon mixture (raffinate I or hydrogenated crack $C_4$ (HCC4)) always remains which contains mainly the saturated hydrocarbons, n-butane and isobutane, and the olefins isobutene, 1-butene and 2-butenes.

The isobutenic hydrocarbon mixtures used in the process according to the present invention may have the following compositions:

Typical composition of selectively hydrogenated CC4 and raffinate I which has been obtained from a C4 cut of a steam cracker (high severity)

| Components | HCC4 | | Raffinate I | |
| --- | --- | --- | --- | --- |
| | min [%] | max [%] | min [%] | max [%] |
| Isobutane | 1 | 4.5 | 1.5 | 8.0 |
| n-butane | 5 | 8 | 6.0 | 15.0 |
| t-butene | 18 | 21 | 7.0 | 10 |
| l-butene | 35 | 45 | 15.0 | 35.0 |
| Isobutene | 22 | 28 | 33.0 | 50.0 |
| c-butene | 5 | 8 | 4.0 | 7.0 |
| 1,2-butadiene | | | | <1% |
| 1,3-butadiene | 500 ppm | 2000 ppm | | <1% |
| Monovinylacetylene | | | | <1% |

Typical composition of raffinate I which is obtained from C4 cuts from catalytic crackers and steam crackers (low severity)

| Components | Raffinate I from catalytic cracker typical [%] | Raffinate I from steam cracker (low severity) typical [%] |
| --- | --- | --- |
| Isobutane | 37 | 3 |
| n-butane | 13 | 6 |
| t-butene | 12 | 10 |
| l-butene | 12 | 27 |
| Isobutene | 15 | 44 |
| c-butene | 11 | 10 |
| 1,3-butadiene | <<1% | <<1% |

Raffinate I or HCC4 is, among others, a preferred isobutenic hydrocarbon mixture for the purposes of this present invention. Since plants for working up $C_4$-hydrocarbons are generally constructed as a series (combination of a plurality of plants), it is possible, however, that the raffinate I or HCC4 runs through one or more other process stages before entry into the process according to the present invention. In this way, it is possible to realize an individually adapted overall plan for workup in each case with the appropriate product portfolio.

Typical process stages which may proceed the process according to the present invention are water scrubbing, purification on absorbers, selective hydrogenation, TBA synthesis and other selective conversions, drying, hydroisomerization and distillation.

Water Scrubbing

Water scrubbing can be used to fully or partly remove hydrophilic components from the isobutenic hydrocarbon mixture, for example nitrogen components. Examples of nitrogen components are acetonitrile or N-methyl-pyrrolidone (which may stem, for example, from 1,3-butadiene extractive distillation). Oxygen compounds (for example acetone from FCC cracker) can also be partly removed by water scrubbing. The isobutenic hydrocarbon stream is saturated after water scrubbing with water. In order to avoid biphasicity in the reactor, the reaction temperature should be approx. 10° C. above the temperature of the water scrubbing.

Adsorbers

Adsorbers are used in order to remove impurities. This may be advantageous, for example, when noble metal catalysts are used in one of the process steps. Often, nitrogen or sulfur compounds are removed by upstream adsorbers. Examples of adsorbers are alumina, molecular sieves, zeolites, activated carbon, clay earths impregnated with metals. Adsorbers are sold by various companies, for example Alcoa (Selexsorb®).

Selective Hydrogenation

Polyunsaturated compounds, in particular 1,3-butadiene, still present in small amounts can optionally be further reduced by further selective hydrogenation steps (cf. EP 081041; Erdöl, Kohle, Erdgas, Petrochem, 1986, 39, 73).

Other Selective Conversions

Selective chemical conversions can be used to fully or partly remove further components from isobutenic mixtures. When 1-butene is present in the mixture, this can, for example, be selectively hydroformylated. The resulting aldehydes (pentanal, 2-methylpentanal) can be removed by distillation.

TBA Synthesis

Portions of the isobutene can be reacted with water to give tert-butanol (TBA). Processes for preparing TBA from isobutenic hydrocarbon mixtures form part of the prior art (cf., for example, Erdöl, Erdgas, Kohle, 1987, 103, 486). TBA is used, for example, as a solvent, but is also used for preparing highly pure isobutene by dissociation to isobutene and water.

Drying

Any water present in the isobutenic hydrocarbon mixture, which may stem, for example, from the water scrubbing or the TBA synthesis, can be removed by existing processes for drying. Suitable processes are, for example, the distillative removal of the water as an azeotrope. It is often possible to utilize an azeotrope with $C_4$-hydrocarbons present, or azeotroping agents are added. The water content of the isobutenic hydrocarbon mixture after drying should be approx. 10–50 ppm. The water content after drying includes all values and subvalues therebetween, especially including 15, 20, 25, 30, 35, 40 and 45 ppm.

Hydroisomerization

The process of hydroisomerization can be used to shift the positions of double bonds in the molecule. The classic example is the hydroisomerization of 1-butene to 2-butenes. At the same time, polyunsaturated compounds (for example residues of 1,3-butadiene) are hydrogenated to simple olefins. Hydroisomerization processes form part of the prior art and, for example, part of the patent applications GB 2,057,006, U.S. Pat. No. 3,764,33 and DE 2223513.

When a hydroisomerization preceding the process according to the present invention alters the ratio of the 1-butene/2-butenes fractions in the feed, this has effects on the formation of the codimers which are formed in the process according to the present invention. It is possible, for example, from isobutenic hydrocarbon mixtures in which the 1-butene content has been reduced by hydroisomerization processes to near to the thermodynamic equilibrium, by dimerization over partly neutralized ion exchangers, to obtain products in which 2,2-dimethylhexenes (codimers of isobutene and 1-butene) are present to a fraction of less than 1%. It is possible to remove highly pure diisobutene by distillation from such mixtures in a purity of >98.5%, preferably >99%, most preferably >99.5%.

Hydroisomerization has gained importance in particular because it is possible in a substantial isomerization of the 1-butene to 2-butene to remove the isobutene with the residues of 1-butene by distillation, optionally together with isobutane, from the remaining $C_4$-hydrocarbons. By elegant combination of distillation and hydroisomerization, for example in a reactive distillation, it is possible in this way to obtain isobutenic streams which are substantially free of n-butenes. These streams are also suitable as a raw material for the process according to the present invention. (EP 1 184 361 describes the use of a raw material obtained in this way for the oligomerization of isobutene, said oligomerization being performed as a reactive distillation). The product of the oligomerization over the partly neutralized ion exchanger is then substantially free of $C_8$ codimers.

Distillation

The isobutenic hydrocarbon mixtures can be separated by distillation into fractions having different isobutene concentrations. This can be effected either directly with the raffinate I or the HCC4, or after one or more other process stages have been run through (cf. hydroisomerization). It is possible by direct distillation of the raffinate I or of the HCC4, for example, to obtain a separation into a 2-butenes- and n-butane-depleted, isobutene-enriched fraction.

The Oligomerization According to the Present Invention

Various embodiments are possible for the industrial implementation of the conversion of the isobutenic hydrocarbon mixtures. The conversion can be carried out batchwise or preferably in continuous reactors which are customarily used in solid/liquid contact reactions. When continuous flow reactors are used, it is usual, but not obligatory, to use a fixed bed. An example of a design other than fixed bed reactors is a reactor in which the ion exchanger is suspended in a liquid phase (cf. "Bayer process", Erdöl und Kohle, Erdgas, Petrochemie, 1974, 27, Volume 5, page 240).

When a fixed bed flow reactor is used, the liquid may flow upward or downward. Preference is usually given to downward flow of the liquid. A cooling liquid flowing around the reactor may, if present, have the same or opposite flow direction. It is also possible to operate the reactor with product recycling or in straight paths.

When tubular reactors are used, the ratio of length to diameter of the catalyst bed may be varied, either via the geometric dimensions of the reactor or via its fill level. At a constant amount of catalyst and LHSV, it is thus possible to achieve different superficial velocities.

The conversion of the isobutenic hydrocarbon mixtures over acidic ion exchangers proceeds with the release of energy, which leads to heating of the reaction mixture. When ion exchangers are used which have not been partly neutralized, moderators which reduce the activity of the catalyst are often required to limit the temperature rise. The moderators used are, for example, alcohols (TBA), ethers (MTBE) or water. A disadvantage of the use of moderators is that they have to be separated from the product stream (cf. Hydrocarbon Processing, February 2002, page 81). Only when they are present in low concentration can they optionally remain in the product.

A further tried-and-tested means for limiting the temperature rise is the dilution of the isobutenic hydrocarbon mixtures, for example by recycling product or by adding inert hydrocarbons, for example diisobutane.

As a result of the catalyst activity reduced by partial neutralization, the reaction rates per unit of catalyst volume are lower than when unexchanged ion exchange resins are used. The lower conversion also reduces the amount of heat generated. In an appropriate reactor design, this allows the heat to be removed to a sufficient extent and the use of moderators to be dispensed with. In a preferred embodiment of the process according to the present invention, moderators are therefore not used.

The reactors used in the industrial process may be operated adiabatically, polytropically or virtually isothermally. Virtually isothermally means that the temperature at an arbitrary point in the reactor is a maximum of 10° C. higher than the temperature at the reactor entrance. In the case of adiabatic operation of the reactors, it is generally sensible to connect a plurality of reactors in series and to cool between the reactors. Reactors which are suitable for polytropic or virtually isothermal operation are, for example, tube bundle reactors, stirred tanks and loop reactors.

The reactor may also be operated in the form of a reactive distillation which contains catalytic structured packings comprising partly neutralized ion exchangers. Examples of catalytic structured packings include Katapack® from Sulzer and Multipack® from Montz GmbH.

It is possible to combine a plurality of reactors, even of different designs. Downstream of each reactor there may optionally be a distillative removal of reaction products. It is additionally possible to operate reactors with recycling of product.

The temperatures at which the oligomerization is to be operated are between 5 and 160° C., preferably between 40 and 110° C. The temperature of the oligomerization includes all values and subvalues therebetween, especially including 10, 15, 20, 25, 30, 35, 40, 45, 50, 55, 60, 65, 80, 75, 80, 85, 90, 95, 100, 105, 110, 115, 120, 125, 130, 135, 140, 145, 150 and 155° C.

The conversion can be effected with and without addition of an additional solvent. The solvents used are preferably saturated hydrocarbons, in particular $C_4$-, $C_8$- or $C_{12}$-hydrocarbons. Very particular preference is given to the use of isooctane. When solvents are added, their proportion is from 0 to 60% by weight, preferably from 0 to 30% by weight. The amount of solvent includes all values and subvalues therebetween, especially including 5, 10, 15, 20, 25, 30, 35, 40, 45, 50 and 55% by weight.

The conversion according to the present invention may be carried out at a pressure equal to or above the vapor pressure of the starting hydrocarbon mixture at the particular reaction temperature, preferably at a pressure of below 40 bar, i.e. the isobutenic hydrocarbon mixtures are fully or partly in the liquid phase during the oligomerization. When the reaction is to be carried out completely in the liquid phase, the pressure should be from 2 to 4 bar higher than the vapor pressure of the reaction mixture, in order to avoid evaporation problems in the reactors.

Even when the reaction is carried out at a pressure at which the reaction mixture is not completely liquid (for example in a reactive distillation or in process variants similar to U.S. Pat. No. 5,003,124), the oligomerization of the process according to the present invention still takes place in the liquid phase, i.e. over "moist" (liquid-wetted) catalyst.

The overall conversion of isobutene can be adjusted via the type and amount of the catalyst used, the reaction conditions employed and the number of reaction stages. It is possible in principle to convert the isobutene in the isobutenic hydrocarbon mixtures virtually quantitatively. When other olefins are present, for example when the raw material used is raffinate I, formation of codimers of isobutene with other olefins can increase markedly. It is therefore advantageous to limit the conversion of isobutene to 95%, even better to 90%.

The effluent of the oligomerization according to the present invention can be worked up in various ways. Preference is given to separating the effluent of the oligomerization into $C_8$-olefins, i.e. namely diisobutene, and $C_4$-olefins, i.e. unconverted olefins such as isobutene, 1-butene and/or 2-butene, and the inert butanes.

A preferred form of the separation of these fractions is distillative separation. This initially removes unconverted isobutene together with further low boilers (fraction (A), hydrocarbons having less than 7 carbon atoms) from the oligomers.

When the raw material used in the process according to the present invention is raffinate I, fraction (A) obtained in the distillation is a mixture which has a composition approaching that of what is frequently referred to as raffinate II. Residues of unconverted isobutene may, if desired, be removed from this mixture by known processes, for example by etherification with alcohols (DE 2853769; Ullmann's Encyclopedia, Sixth Edition, Electronic Release, Methyl tert-butyl ether-Production).

The isobutene still present in the $C_4$-olefinic fraction may optionally be etherified with an alcohol in at least one further reaction stage. For this purpose, preference is given to using methanol or ethanol to obtain MTBE or ETBE.

The remaining isobutene can also be reacted with alcohols to give ethers before the distillative separation. An appropriate process is described in DE 2944457. The oligomerization effluence is reacted with alcohols, preferably methanol, over acidic catalysts. This forms a tert-butyl ether from the isobutene still present. It is then possible, for example, to remove a raffinate II from this mixture which optionally still contains small amounts of alcohol by distillation and further process it.

It is possible to obtain 1-butene of high purity from raffinate II which still contains small amounts of isobutene (Ullmann's Encyclopedia, Sixth Edition, Electronic Release, Butenes—Upgrading of Butenes). Other use possibilities for raffinate II are the oligomerization of the butenes present, for example over heterogeneous nickel catalysts. This provides, inter alia, di-n-butene from which plasticizers (for example diisononyl phthalate) for plastics can be prepared by hydroformylation, hydrogenation and esterification.

After the removal of isobutene together with further low boilers (fraction (A), hydrocarbons having less than 7 carbon atoms), a fraction which contains mainly $C_8$-hydrocarbons is obtained. In addition to diisobutene, this also contains codimers and higher oligomers ($C_{12}$, $C_{16}$). This fraction may be further fractionated in further distillation steps. For example, it is possible to remove a fraction of highly pure diisobutene, in order to use this separately, for example for chemical syntheses. For use as a carburetor fuel component, it may be necessary to remove high-boiling components (boiling point preferably >220° C.).

It is also possible to hydrogenate all or some of the $C_8$-olefin-containing fraction to the saturated hydrocarbons.

When etherification of the isobutene still present is carried out before the removal of the low boilers, the fraction of the oligomers of isobutene, in addition to the oligomers, also contains ether and residues of alcohol. This mixture can be separated by distillation using known processes into individual fractions (whose main constituents are, for example, ether or alcohol or oligomers). One or more of these fractions ($C_n$) may be used, for example, as a fuel additive.

For use as a carburetor fuel component, it may be advantageous to fully or partly hydrogenate the olefinic double bonds of the oligomers.

Methods for hydrogenating the products of the oligomerization to the corresponding paraffins are sufficiently well known to those skilled in the art. Common methods for hydrogenating olefins are described, for example, in F. Asinger, "CHEMIE UND TECHNOLOGIE DER MONOOLEFINE", AKADEMIE VERLAG, BERLIN, 1957, page 626–628 or DE 197 19 833.

In a preferred embodiment, the hydrogenation is carried out in the liquid phase over a heterogeneous hydrogenation catalyst. The hydrogenation catalysts used are preferably Pt, Pd and Ni on inorganic support materials. The temperature at which the hydrogenation is carried out is preferably in the range from 10 to 250° C., and the pressure is between 1 bar and 100 bar. The temperature of the hydrogenation includes all values and subvalues therebetween, especially including 20, 30, 40, 50, 60, 70, 80, 90, 100, 110, 120, 130, 140, 150, 160, 170, 180, 190, 200, 210, 220, 230 and 240° C. The pressure of the hydrogenation includes all values and subvalues therebetween, especially including 5, 10, 15, 20, 25, 30, 35, 40, 45, 50, 55, 60, 65, 70, 75, 80, 85, 90 and 95 bar.

After the hydrogenation, further fractions can be obtained by distillative separation. It is possible by blending to obtain fuel additives of certain properties from these and from unhydrogenated fractions.

The examples which follow are intended to further illustrate the present invention, but not restrict its field of application as evident from the patent claims.

Having generally described this invention, a further understanding can be obtained by reference to certain specific examples which are provided herein for purposes of illustration only, and are not intended to be limiting unless otherwise specified.

EXAMPLES

Example 1

Preparation of a Partly Neutralized Catalyst, Adjustment of the Acid Capacity

The Rohm and Haas ion exchanger used (Amberlyst 15) had an original acid capacity of 1.43 mol of $H^+/l$. To attain the desired activity, 50% of the acidic centers were neutralized.

For this purpose, 1000 ml of the ion exchange resin were slurried in 1000 ml of deionized water and a solution of 28.6 g of sodium hydroxide (0.715 mol) and 500 ml of deionized water were added dropwise with vigorous stirring within the temperature range from 20 to 40° C. in one hour. Stirring was continued for 5 min and the ion exchange resin afterwards washed to neutrality with three times 1000 ml of deionized water. The subsequent capacity measurement of the partly neutralized ion exchanger was 0.715+/−0.03 mol of $H^+/l$. The catalyst was dried at 70° C. for 15 h.

Other partly neutralized ion exchange resins were prepared in a similar manner to example 1 by reacting the acidic ion exchange resin suspended in water with the calculated amount of an aqueous alkali metal hydroxide solution.

The oligomerization experiment (Examples 2 to 6) were carried out in a jacketed laboratory tubular reactor of length 2 m and internal diameter of 6 mm. The reactor could be heated with the aid of a heat carrier oil which was pumped through the reactor jacket. In all experiments, an isobutane-isobutene mixture was oligomerized at 22 bar.

Examples 2 to 4

In experiments 2–4, 54 ml of a (dried) Amberlyst 15 ion exchanger partly neutralized with $Na^+$ were used in each case. The degree of exchange of the protons was in each case checked by a determination of the capacity of the ion exchanger.

The isobutene was oligomerized in each case in a tubular reactor of length 200 cm (wound to a spiral), internal diameter 6 mm, which was charged with the catalyst. The tube was heated from outside by an oil bath. The raw material was conveyed through the reactor by a pump; the pressure is controlled at the exit of the reactor to a constant 22 bar by a pressure regulator.

The operating conditions of the individual experiments, analyses of feed and effluent are reported in the following table. The temperature was adjusted in such a way as to result in comparable isobutene conversions.

In the series, it can be clearly seen that the partial neutralization of the ion exchanger allows distinctly improved selectivities for the C8 products to be achieved at comparable conversions.

|  |  | Experiment No. | | |
| --- | --- | --- | --- | --- |
|  |  | 2 | 3 | 4 |
| Ion exchanger |  | A15 | A15 | A15 |
| Degree of exchange, metal |  | 0% | 10%, Na | 40%, Na |
| Temp. | [° C.] | 40.0 | 51.2 | 110.0 |
| Feed | [kg/h] | 0.502 | 0.526 | 0.510 |
| Feed analysis |  |  |  |  |
| Isobutane | [%] | 2.20 | 4.09 | 2.88 |
| n-butane | [%] | 9.56 | 12.16 | 8.98 |
| trans-butene | [%] | 9.17 | 8.74 | 8.71 |
| 1-butene | [%] | 27.71 | 26.56 | 28.33 |
| Isobutene | [%] | 44.76 | 41.99 | 45.14 |
| cis-butene | [%] | 6.12 | 5.98 | 5.46 |
| Remainder | [%] | 0.49 | 0.46 | 0.49 |
| Effluent analysis |  |  |  |  |
| Isobutane | [%] | 2.57 | 4.31 | 3.28 |
| n-butane | [%] | 10.90 | 13.68 | 10.22 |
| trans-butene | [%] | 10.43 | 10.14 | 10.43 |
| 1-butene | [%] | 31.68 | 29.22 | 30.79 |
| Isobutene | [%] | 37.03 | 35.07 | 37.93 |
| cis-butene | [%] | 6.88 | 7.06 | 6.87 |
| Remainder | [%] | 0.52 | 0.50 | 0.48 |
| Isobutene conversion |  | 27.4% | 25.8% | 26.2% |
| Selectivities |  |  |  |  |
| Sel C8 | [%] | 84.9 | 88.68 | 92.66 |
| Sel C12 | [%] | 11.6 | 9.8 | 7.1 |
| Sel C16+ | [%] | 3.5 | 1.31 | 0.07 |
| 2,4,4-TMP in the C8 | [%] | 94.9 | 95.4 | 95.7 |

Examples 5 and 6

In experiments 5 and 6, the raw material used was in each case an isobutenic mixture of C4 hydrocarbons. The composition is reported in the following table.

|  | | Experiment No. | |
|---|---|---|---|
|  | | 5 | 6 |
| Ion exchanger | | A15 | A15 |
| Degree of exchange, metal | | 40%, Na | 0%, Na |
| Feed analysis | | | |
| Isobutane | [%] | 0.01 | 0.03 |
| n-butane | [%] | 9.25 | 10.82 |
| trans-butene | [%] | 19.25 | 17.16 |
| l-butene | [%] | 11.79 | 14.45 |
| Isobutene | [%] | 50.72 | 49.55 |
| cis-butene | [%] | 8.83 | 7.96 |
| Remainder | [%] | 0.15 | 0.05 |

In experiment 5, 54 ml of a Amberlyst 15 ion exchanger 40% neutralized with sodium ions were used, and in experiment 6 54 ml of an unneutralized Amberlyst 15 ion exchanger (in each case dried ion exchanger). The degree of exchange of the protons in experiment 5 was checked by a determination of the capacity of the ion exchanger.

The experiments were carried out in a similar manner to Examples 2 to 4.

At a feed rate of 500 g/h, the conversion of the isobutene (i-bene conversion) was changed by varying the reaction temperature between 50 and 120° C. In addition to the conversion, the selectivity from C8-hydrocarbons (C8-sel.) and the content of 2,4,4-trimethylpentenes (2,4,4-TMP) in the C8 fraction were in each case determined by gas chromatography.

| Analysis No. | i-bene conversion [%] | C8 sel. [%] | 2,4,4-TMP [%] |
|---|---|---|---|
| 5-a | 57.69 | 85.33 | 93.60 |
| 5-b | 63.82 | 81.71 | 93.47 |
| 5-c | 74.36 | 77.23 | 93.81 |

| Analysis No. | i-bene 875 conversion | C8 sel. [%] | 2,4,4-TMP [%] |
|---|---|---|---|
| 6-a | 57.49 | 78.79 | 94.30 |
| 6-b | 63.76 | 76.30 | 93.50 |
| 6-c | 74.66 | 71.61 | 90.43 |

It has been shown that distinctly better C8 selectivities can be achieved with the partly neutralized ion exchanger at comparable isobutene conversions.

German patent application 10235934.2 filed Aug. 6, 2002, and German patent application 10306214.9 filed Feb. 13, 2003, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for oligomerizing isobutene, comprising:
   oligomerizing isobutene in the presence of n-butene over a solid, acidic ion exchanger having acidic protons; wherein at least one acidic proton of said ion exchanger has been exchanged for a metal ion.

2. The process according to claim 1, wherein from 0.1 to 30% of said acidic protons of the ion exchanger have been exchanged for metal ions.

3. The process according to claim 1, wherein an isobutenic hydrocarbon mixture comprising isobutene, 1-butene, 2-butene and butanes is used for said oligomerizing.

4. The process according to claim 1, wherein the metal ions are ions selected from the group consisting of alkali metals, alkaline earth metals, rare earth metals and mixtures thereof.

5. The process according to claim 3, wherein said isobutenic hydrocarbon mixture is at least partially in the liquid phase during said oligomerizing.

6. The process according to claim 1, wherein said oligomerizing is carried out at a temperature of from 5 to 160° C.

7. The process according to claim 3, wherein less than 5 mol% of said 1-butene is isomerized to 2-butene.

8. The process according to claim 1, wherein an effluent of said oligomerizing is fractionated into $C_8$-olefins and $C_4$-olefins.

9. The process according to claim 8, wherein isobutene is present in said $C_4$-olefinic fraction; and
   wherein said isobutene is etherified with an alcohol in at least one further reaction stage.

10. The process according to claim 8, wherein the $C_8$-olefinic fraction is hydrogenated to give saturated hydrocarbons.

11. The process according to claim 1, wherein said ion exchanger is a solid sulfonated ion exchange resins in which from 0.1 to 60% of the acidic protons of the sulfonic acid groups have been exchanged for metal ions.

12. The process according to claim 1, wherein an ion exchange capacity of said ion exchange resin is between 1 and 2 mol.

13. The process according to claim 1, wherein a pore volume of said ion exchange resin is from 30 to 60 ml/g.

14. The process according to claim 1, wherein a particle size of said ion exchange resin is between 500 μm and 1500 μm.

15. A process for preparing 1-butene from $C_4$-hydrocarbon comprising:
   converting a $C_4$-hydrocarbon mixture over an acidic, solid ion exchanger having acidic protons;
   wherein at least one acidic protons of said ion exchanger has been exchanged for a metal ion, thereby obtaining a reaction product; and
   wherein the 1-butene is removed from the reaction product by distillation.

16. The process of claim 15, wherein from 0.1 to 30% of said acidic protons of the ion exchanger have been exchanged for metal ions.

17. The process of claim 16, wherein the $C_4$-hydrocarbon mixture comprising at least one component selected from the group consisting of isobutene, 1-butene, 2-butene, butanes is used for oligomerizing.

* * * * *